United States Patent
Brody et al.

[11] Patent Number: 5,922,210
[45] Date of Patent: Jul. 13, 1999

[54] TANGENTIAL FLOW PLANAR MICROFABRICATED FLUID FILTER AND METHOD OF USING THEREOF

[75] Inventors: James P. Brody, Seattle; Thor D. Osborn, Carnation, both of Wash.

[73] Assignee: University of Washington, Seattle, Wash.

[21] Appl. No.: 08/665,218

[22] Filed: Jun. 14, 1996

Related U.S. Application Data

[60] Provisional application No. 60/000,281, Jun. 16, 1995.

[51] Int. Cl.[6] .......................... B01D 35/00; B01D 37/00; G01N 33/48
[52] U.S. Cl. ................. 210/767; 210/416.1; 210/422; 210/433.1; 422/50; 422/68.1; 422/101; 435/2; 436/177
[58] Field of Search ................... 210/85, 416.1, 210/422, 433.1, 435, 650, 739, 767; 435/2; 422/101, 50, 68.1; 436/177

[56] References Cited

U.S. PATENT DOCUMENTS

| | | | |
|---|---|---|---|
| 4,212,742 | 7/1980 | Solomon et al. | 210/247 |
| 4,751,003 | 6/1988 | Raehse et al. | 210/639 |
| 4,753,776 | 6/1988 | Hillman et al. | 422/101 |
| 4,797,211 | 1/1989 | Ehrfeld et al. | 210/321.84 |
| 4,801,379 | 1/1989 | Ehrsam et al. | 210/498 |
| 5,304,487 | 4/1994 | Wilding et al. | 422/55 |
| 5,338,400 | 8/1994 | Jerman | 156/647 |
| 5,498,392 | 3/1996 | Wilding et al. | 422/68.1 |
| 5,587,128 | 12/1996 | Wilding et al. | 422/50 |
| 5,635,358 | 6/1997 | Wilding et al. | 435/7.2 |
| 5,726,026 | 3/1998 | Wilding et al. | 435/7.21 |

FOREIGN PATENT DOCUMENTS

| | | |
|---|---|---|
| WO 79/01120 | 5/1979 | WIPO . |
| WO 93/22053 | 11/1993 | WIPO . |
| WO 95/13860 | 5/1995 | WIPO . |
| 96/14934 | 5/1996 | WIPO . |
| 96/15576 | 5/1996 | WIPO . |

OTHER PUBLICATIONS

Kittisland, G., and Stemme, G. (1990), "A Sub–micron Particle Filter in Silicon," *Sensors and Actuators*, A21–A23:904–907.
Stemme, G. and Kittisland G. (1988), "New fluid filter structure in silicon fabricated using a self–aligning technique," *Appl. Phys. Lett.* 53:1566–1568.
Gravesen, P., et al. (1993), "Microfluidics—a review," *J. Micromech. Microeng.* 3:168–182.
Wallis, G. and Pomerantz, D.I. (1969) *J. Appl. Physics* 40:3946–3949.
Shoji, S. and Esashi, M. (1994), "Microflow devices and systems," *J. Micromechanics and Microengineering* 4:157–171.
Reisman, A., et al. (1979), "The Controlled Etching of Silicon in Catalyzed Ethylenediamine–Pyrocatechol–Water Solutions," *J. Electrochem. Soc.* 126:1406–1415.
Wilding, P., et al. (1994), "Manipulation and Flow of Biological Fluids in Straight Channels Micromachined in Silicon,", *Clin. Chem.* 40:43–47.

*Primary Examiner*—John Kim
*Attorney, Agent, or Firm*—Greenlee, Winner and Sullivan, P.C.

[57] ABSTRACT

A microfilter utilizing the principles of tangential flow to prevent clogging, and sloped channel sides to overcome surface tension effects is provided which has feed inlet and exit connected by a feed flow channel, a barrier channel parallel to the feed flow channel, and a filtrate collection channel parallel to the barrier channel so that liquid can flow from the feed flow channel through the barrier channel which is too small to accommodate the particles, into the filtrate collection channel, and from then through a filtrate flow channel to a filtrate exit. Several picoliters of cell-free plasma are recovered from one drop of blood for analysis.

20 Claims, 1 Drawing Sheet

TANGENTIAL FLOW PLANAR MICROFABRICATED FLUID FILTER AND METHOD OF USING THEREOF

This is a utility patent application taking priority from provisional patent application 60/000,281 filed Jun. 16, 1995, which is incorporated herein by reference.

This invention was made with government support under Army research contract DAMD17-94-J-4460 awarded by the U.S. Army. The government has certain rights in the invention.

FIELD OF THE INVENTION

This invention relates generally to microfilters useful, for example, for separating plasma from whole blood. Analyzable quantities of plasma, i.e., from about 1 picoliter to a few hundred nanoliters, can be separated from one drop of whole blood within a few seconds by microfilters of this invention.

BACKGROUND OF THE INVENTION

Many blood tests must be performed on plasma without cellular matter present. In the standard laboratory protocol, pure plasma is obtained through centrifugation. In order to produce a miniaturized blood sensor, a method to separate plasma other than centrifugation is needed.

Chemical analysis of biological samples is constrained by sample size. Withdrawing a few milliliters of blood from an adult may have little effect, but repeating this procedure every hour or even withdrawing this amount once from an infant can significantly alter the health of the subject. For these reasons, a miniaturized blood analysis system would be useful. Furthermore, while many sophisticated tests that have great importance for critical care can be performed in major hospital laboratories, a substantial impact could be made on the practice of emergency medicine if some key tests could be performed on the patient at the site of injury.

Microfabricated fluid filters exist in the literature; however, these lack the advantages of the microfilter of the present invention.

Kittisland, G., and Stemme, G. (1990), "A Sub-micron Particle Filter in Silicon," Sensors and Actuators, A21–A23:904–907; and Stemme, G. and Kittisland, G. (1988), "New fluid filter structure in silicon fabricated using a self-aligning technique," Appl. Phys. Lett. 53:1566–1568, describe microfilters fabricated using a silicon wafer and capable of filtering out particles down to 50 nm. This filter design cannot be etched into the surface of a silicon wafer. Further, although these filters seem to perform well for gases, surface tension causes problems when filtering liquids. Gravesen, P., et al. (1993), "Microfluidics—a review," J. Micromech. Microeng. 3:168–182.

Wilding, P., et al. (1994), "Manipulation and Flow of Biological Fluids in Straight Channels Micromachined in Silicon," Clin. Chem. 40:43–47 disclose microfilters useful for separating blood cells from plasma etched into silicon wafers using a photolithographic process. These filter designs do not allow tangential or crossflow of the feed material past the barrier, which may be a narrower channel or barrier posts, to clear the barrier of particles. Further, in all cases, pressure must be applied to the system to obtain analyzable quantities of plasma. Because the minimum dimension of these filters is determined by a photolithographic process, they have a limit of about 1 micron. The photolithographic process is more sensitive to defects and requires tighter constraints on manufacturing than a process that relies on etching time to define the size of the channels as is used herein.

Wilding, P., et al. U.S. Pat. No. 5,304,487 issued Apr. 19, 1994 discloses mesoscale analytical devices for fluid handling comprising flow channels and fluid handling regions micromachined into silicon wafers. Again, no microfilters having tangential flow capabilities to aid in keeping the barrier free of particles are disclosed.

Raehse, W., et al. U.S. Pat. No. 4,751,003 issued Jun. 14, 1988 discloses a microfilter using a crossflow principle having polysulfone tubes with micropore diameters of 0.3 to 0.5 microns disposed in a cylindrical configuration. Ehrfeld, W. et al. U.S. Pat. No. 4,797,211 issued Jan. 31, 1989 discloses a crossflow microfilter comprising a microporous membrane having slit-shaped cross-sections. Solomon, H., et al. U.S. Pat. No. 4,212,742 issued Jul. 15, 1980 discloses a filtration apparatus for separating blood cells from liquids utilizing crossflow principles comprising multiple layers and membrane filters.

Ehrsam, C. et al. U.S. Pat. No. 4,801,379 issued Jan. 10, 1989 discloses a microfilter made of a foil having pores set into protuberances on the foil to aid in prevention of clogging. Hillman, R. U.S. Pat. No. 4,753,776 issued Jun. 28, 1988 discloses a microfilter useful for separating plasma from red blood cells comprising glass fibers using capillary action to promote flow.

Shoji, S. and Esashi, M. (1994), "Microflow devices and systems," J. Micromechanics and Microengineering 4:157–171, provide a general review of microvalves, micropumps, microflow sensors and integrated flow systems.

None of the foregoing references disclose or suggest the microfilter design disclosed herein which provides for tangential flow, ease and control of manufacturing, and minimization of surface tension problems.

All patents and publications referenced herein are incorporated by reference herein in their entirety.

SUMMARY OF THE INVENTION

This invention provides a microfilter useful for treating a feed liquid to separate liquid from particles contained therein comprising the following elements:

a) a feed inlet;

b) a feed exit;

c) a feed flow channel having a minimum dimension sufficient to permit flow of the particles and liquid therethrough, disposed between and in fluid communication with the feed inlet and the feed exit;

d) a filtrate collection channel parallel to the feed flow channel;

e) a barrier channel parallel to, between, and in fluid communication with the feed flow channel and the filtrate collection channel; the barrier channel having a minimum dimension sufficiently small to permit flow of the liquid but not the particles therethrough;

f) a filtrate exit in fluid communication with the filtrate collection channel;

wherein the elements are formed into the surface of a horizontal substrate; and wherein the surface of the horizontal substrate is covered by a lid.

Preferably the microfilter also comprises a filtrate outlet channel connecting the filtrate collection channel and the filtrate exit.

Methods for making and using the microfilters of this invention are also provided.

DETAILED DESCRIPTION OF THE PREFERRED EMBODIMENTS

Figure 1:
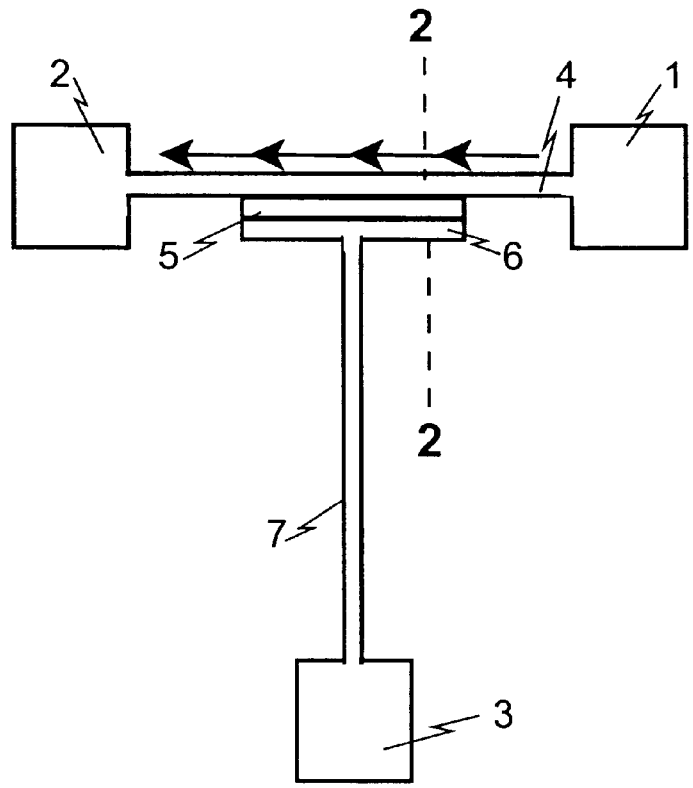
FIG. 1 is a schematic diagram of a filter design of this invention (not to scale).

FIG. 1 shows a microfilter of this invention comprising a feed inlet 1 depicted as a square port, a feed exit 2 depicted as a square port, a filtrate exit 3 depicted as a square port, a feed flow channel 4 connecting the feed inlet 1 and feed exit 2, a barrier channel 5 disposed between the feed flow channel 4 and filtrate collection channel 6, and a filtrate outlet channel 7 connecting the barrier channel 5 with the filtrate exit 3.

Feed liquid containing particles enters at feed inlet 1 at the upper right and flows to feed exit 2 at the upper left. Some particle-free fluid is pushed across barrier channel 5 into filtrate collection channel 6 and from thence down to filtrate exit 3 through filtrate outlet channel 7. By controlling the pressure drop between the feed inlet 1 and the filtrate exit 3, it is possible to control how quickly and how much filtrate is drawn out. Shear forces in the feed flow channel 4 act to prevent clogging of barrier channel 5 by particles.

Figure 2:
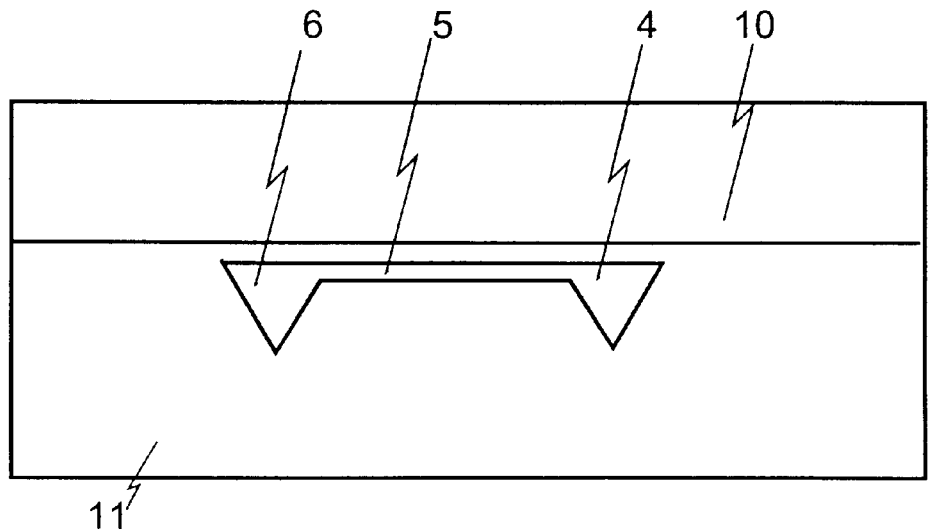
FIG. 2 is a cross section taken along line 2—2 of FIG. 1 showing the feed flow channel, barrier channel and filtrate collection channel of a microfilter of this invention.

FIG. 2 is a cross section (not to scale) taken along line 2—2 of FIG. 1 showing feed flow channel 4, barrier channel 5 and filtrate collection channel 6 as well as substrate 11 and lid 10. The channels in the silicon substrate are etched using an anisotropic etchant to give characteristic V-shaped grooves. The corners between feed flow channel 4 and feed inlet 1, between feed flow channel 4 and feed exit 2, and between filtrate collection channel 6 and filtrate exit 3 are not actually as sharp as shown, resulting in an enlargement of the cross-section of the channels as they interface with the inlet and exits, which is critical to preventing surface tension lock in the absence of pressurization of the system. The barrier channel is etched in a different step from the flow channels and can be anywhere from 0.010 micron to a few microns deep. The lid is preferably Pyrex glass attached to the substrate by anodic bonding, as is known in the art. In practice, the lid may have a tendency to bow in and may tend to close off channels such as barrier channel 5 which may be less than one micron deep. To solve this problem, spacers may be designed in the barrier channel by etching the channel to leave unetched bridges across it. Preferred spacers are about 10 microns long, placed at 30 micron intervals across the width of barrier channel 5.

The term "microfilter" means a filter capable of separating fluid from particles down to 0.1 microns or less in size (average diameter). Thus the barrier channel may have a depth less than 0.1 micron, i.e., at least sufficiently small that 0.1 micron particles are unable to flow therethrough. In another embodiment, the barrier channel has a depth of about 0.01 micron so that particles down to near 0.010 micron in size are unable to flow through. The flow channels preferably have depths from about 0.1 micron up to about 300 microns, and widths preferably from about 0.1 micron to about 500 microns, although they may be wider if desired. The microfilters of this invention are designed to handle small quantities, e.g. less than about 10 microliters, and preferably about 1 microliter (less than one drop) of feed liquid and are capable of providing filtrate in analyzable quantities, such as picoliter and nanoliter amounts, e.g., between about one picoliter and about 500 nanoliters, when one microliter of feed liquid is used.

The feed liquid may be any liquid comprising particles too large to flow through the barrier channel. Preferably the feed liquid is blood, the liquid to be separated is plasma, and the particles are blood cells. Red blood cells are disk-shaped, about 2 microns thick and about 8 microns in diameter. White blood cells are irregularly shaped, averaging about 15 microns in diameter. Cell-free plasma is produced at the filtrate exit. Preferably the liquid is a polar liquid, more preferably an aqueous liquid. The microfilter may be designed for use with polar or nonpolar liquids. The surfaces of the microfilter should be treated, as is known to the art, to render them hydrophilic or hydrophobic such that they will be wetted by the type of feed liquid used.

The microfilters of this invention are capable of separating an analyzable quantity of liquid from a feed liquid containing particles which are too large to pass through the barrier channel. It is not necessary that the microfilters of this invention be capable of removing all the particles present in all the feed liquid, only that a sufficient quantity of filtrate free of larger particles be delivered from the filtrate exit of the microfilter to permit analysis thereof. The desired output of the microfilters of this invention is a quantity of liquid from which particles have been removed, rather than the particles themselves or the full amount of the feed liquid.

The feed inlet 1 may be any size and shape capable of receiving sufficient feed liquid to provide an analyzable quantity of filtrate liquid. The feed inlet may be a feed inlet port as shown in FIG. 1, etched into the horizontal substrate as depicted in FIG. 1; however, the feed inlet may be part of another connected device used for previous handling of the feed liquid, e.g., heating, separation, mixing, etc. Preferably the feed inlet is a square-shaped hollow etched completely through the silicon wafer of the preferred embodiment, about 1 mm by 1 mm, having approximately the same depth as the feed flow channel. Connections with other devices are then made from the rear of the wafer. Because of the etching process used in the preferred embodiment in which the etchant attacks the {100} planes of the silicon substrate, the feed inlet 1 of the microfilter of FIG. 1 will have sides sloping at an angle of about 55 degrees.

The feed exit 2 may similarly be of any size and shape convenient for collection of feed liquid from which some or none of the particles and some of the liquid have been removed and may be part of a connected device used for further handling or disposal of the feed liquid. The feed exit 2 may be a feed exit port as shown in FIG. 1 of the same size and shape as the feed inlet 1.

The feed flow channel 4 connecting the feed inlet 1 and the feed exit 2 should have a narrowest dimension wide enough to accommodate the particles in the feed liquid as it flows from the feed inlet 1 to the feed exit 2 past the barrier channel 5, and to provide a flow velocity under the influence of capillary action sufficient to provide a Reynolds number less than that at which inertial effects are negligible, as is more fully discussed hereinafter. In a preferred embodiment hereof, the feed flow channel 4 has a width of about 50 to about 200 microns, a depth of about 50 to about 200 microns, and is substantially V-shaped. However, the feed flow channel can be as wide and deep as desired.

A filtrate collection channel 6 runs generally parallel to the feed flow channel 4. The filtrate collection channel 6 preferably is as long as possible to maximize the throughput, and together with filtrate outlet channel 7 should have a volume large enough to collect an analyzable quantity of filtrate. Preferably, the filtrate collection channel 6 is a few millimeters long, e.g., about 3–5 mm, and of the same depth, width and shape as the feed flow channel 4, although it may be a wide pool or reservoir. It may be any shape capable of holding the collected filtrate.

The feed flow channel 4 and the filtrate collection channel 6 are separated from each other by a barrier channel 5 having a smaller minimum dimension than the feed flow channel 4 such that liquid may pass from the feed flow channel 4 and flow into the barrier channel 5 and from there into the filtrate collection channel 6, but the particles desired to be separated from the feed liquid remain in the feed flow channel 4. The barrier channel 5 is of a length sufficient to allow flow of sufficient liquid for analysis from the feed flow channel 4 even in the absence of system pressurization. Preferably, the barrier channel is the same length as the filtrate collection channel 6. In a preferred embodiment, the barrier channel 5 is about the same width as the feed flow channel 4, although it may be wider to provide greater ease of fabrication consistent with facilitating throughput. The barrier channel 5 may have a depth of less than about 0.1 micron down to about 0.010 micron, and preferably has a depth about 0.5 micron or less. This will preclude blood cells having a maximum dimension of about 8 microns or larger from passing through the barrier channel. The barrier channel 5 is generally too shallow to have the substantially V-shaped profile of the flow channels.

Where no external pressure is present, the surface tension of the fluid alone should be enough to provide initial wetting of the device. This initial wetting provides some flow across the barrier channel 5 and hence some particle-free fluid in filtrate collection channel 6. To prevent surface tension lock, it is important to provide for gradual changes in the curvature of the fluid/air interface. Where there is an abrupt change in the diameter of a channel (from narrow to wide), fluid will not flow through by means of capillary action alone; however, if the diameter change is gradual, capillary action will cause sufficient fluid flow through the filter to produce analyzable quantities of filtrate. The etching process of this invention provides gradual widening of feed flow channel 4 as it connects with the feed inlet 1 so as to prevent surface tension lock, and provides gradual widening of filtrate outlet channel 7 as it connects with filtrate exit 3 to prevent surface tension lock.

The arrangement of the barrier channel 5 with respect to the feed flow channel 4 provides a tangential flow of the feed liquid past the barrier channel which tends to avoid clogging of the barrier channel, as the particles are swept into the flow of the feed material toward the feed exit.

The filtrate collection channel 6 is preferably the same length as the barrier channel 5 and is in fluid communication with it along its entire length to allow maximum flow of filtrate liquid toward the filtrate exit 3.

The filtrate exit 3 has a volume sufficient to accommodate an analyzable quantity of filtrate as discussed above. Again, the filtrate exit 3 can be part of a connected device such as a device for performing a separation, heating, mixing, or analytical step, for example as described in Wilding et al., U.S. Pat. No. 5,304,487. Preferably, the filtrate exit 3 is a filtrate exit port as shown in FIG. 1 of the same size and shape as feed inlet 1.

The filtrate exit 3 is in fluid communication with the filtrate outlet channel 7 preferably by means allowing free flow of filtrate into the filtrate exit 3 in the absence of pressurization of the system. In other words, the surface tension of the filtrate flowing into the filtrate exit 3 must be capable of being overcome by the pressure exerted by capillary action alone. The filtrate may be removed from filtrate collection channel 6 by any means known to the art. The filtrate collection channel 6 may comprise the filtrate exit point. Preferably, the filtrate exit 3 is connected to the filtrate collection channel 6 by a filtrate outlet channel 7 having a conformation which permits free flow of the filtrate therethrough against the force exerted by surface tension, e.g., gradual changes in curvature rather than sharp edges. As more fully discussed hereinafter, the etching process used to form the substantially V-shaped channels of this invention results in a gradual widening of the channels sufficient to overcome the force of surface tension as discussed above.

The microfilter of this invention is capable of being formed on a substrate by microfabrication techniques known to the art, preferably by etching the flat surface of a silicon wafer and cutting to form a device about 1 cm by about 1 cm, and about 300 microns thick. Preferably these are {100} wafers (n-type or p-type) having at least about 100 to about 500 nm of silicon dioxide grown on the surface.

The length of the channels is between about 1 micron and several millimeters, and the depth anywhere from about 0.010 micron to the thickness of the wafer, e.g., about 300 microns. The width may be about 0.1 micron to about 500 microns.

The microfilter of this invention is completed by the addition of a lid placed over the surface of the substrate, touching the raised portions, and providing a top surface for enclosing the channels and ports. Preferably this lid is transparent, and more preferably is glass bonded to the surface of the substrate.

Means for applying pressure to the flow of the feed liquid through the device may also be provided. Such means may be provided at the feed inlet, the filtrate exit (as vacuum), or both. Means for applying such pressure are known to the art, for example as described in Shoji, S. and Esashi, M. (1994), "Microflow devices and systems," J. Micromechanics and Microengineering, 4:157–171, and include the use of a column of water or other means of applying water pressure, electroendoosmotic forces, optical forces, gravitational forces, and surface tension forces. Pressures from about $10^{-6}$ psi to about 10 psi may be used, depending on the requirements of the system. Preferably about $10^{-3}$ psi is used when pressure is required.

When it is desired to reuse the microfilters of this invention, means for providing backflow of fluid across the barrier channel 5 to clear the particles therefrom may be provided. Pressurizing the filtrate exit 3 to about half the pressure being put on the feed inlet 1 generally provides sufficient backflow to clear the device.

In a preferred embodiment of this invention, microfilters of this invention have hydrophilic surfaces to facilitate flow of liquid therein and allow operation of the device without the necessity for pressurization. The substrate may be treated by means known to the art following fabrication of the channels, to render it hydrophilic. The lid is also preferably treated to render it hydrophilic.

The preferred process for making microfilters of this invention comprises:
  a) providing a {100} silicon wafer;
  b) etching a feed flow channel and a filtrate collection channel into the silicon wafer of step a) with an etchant capable of attacking the {100} planes of said silicon wafer to form substantially V-shaped channels; and
  c) etching a barrier channel into said silicon wafer.

A {100} silicon wafer is one in which the major surfaces are substantially {100} planes, although sometimes the orientation in these commercially available wafers is not precise. The etching is preferably done using EPW F-etch as described in Reisman, A., et al. (1979), J. Electrochem. Soc. 126:1406–1415, or another etchant capable of forming substantially V-shaped channels such as potassium hydroxide in a mixture of water and isopropyl alcohol. Preferably the etching is done in three stages, timed to provide the required depth for the channels and ports. In the embodiment of FIG. 1, the inlet and exit ports are preferably etched in a first step, flow channels are preferably etched in a second step, and the barrier channel, which is the shallowest, is preferably etched in a third step. As is understood by those skilled in the art, the previously-etched structures are deepened during subsequent etching steps.

A lid, preferably a glass sheet, is then bonded to the etched substrate to complete the enclosure of the ports and channels. In a preferred embodiment, the substrate and lid are first treated to render them hydrophilic.

In use, a liquid, preferably about one microliter of blood, is injected into the feed inlet 1. The liquid moves through the filter by capillary action and several picoliters of filtrate collect at the filtrate exit 3 for analysis.

Means for injecting feed liquid into the device are provided, as when the microfilter of this invention is used as part of an analytical system. Such means include standard syringes and tubes. Means for removing fluid from the filtrate exit 3 may also be provided, including receptacles for the fluid, inducing flow by capillary action, pressure, gravity, and other means known to the art as described above. Such receptacles may be part of an analytical or other device for further processing the filtrate.

Analysis of the filtrate may be by optical means known to the art such as absorption spectroscopy or fluorescence, by chemical or immunological means, or other means known to the art to detect the presence of an analyte such as a virus, DNA sequence, antigen, microorganism or other factor.

The manufacturing process of this invention minimizes the number of mask steps and wafer/wafer or wafer/glass bonding steps. In manufacturing the microfilters of this invention, size scaling is also considered. Fluid dynamic behavior is directly related to the Reynolds number of the flow. In microdevices, if the velocity decreases as the channel length (where the device is assumed to work in a fixed time at all scales), then the Reynolds number varies in proportion to the square of the length. As devices are miniaturized, the Reynolds number is inevitably reduced.

The Reynolds number is the ratio of inertial forces to viscous forces. As the Reynolds number is reduced, flow patterns depend more on viscous effects and less on inertial effects. Below a certain Reynolds number, e.g. 0.1 (based on lumen size for a system of channels with bends and lumen size changes), inertial effects can essentially be ignored. The microfluidic devices of this invention do not require inertial effects to perform their tasks, and therefore have no inherent limit on their miniaturization due to Reynolds number effects. Applicants' filter designs, while significantly different from previous reported designs, operate in this range.

The devices of the preferred embodiment of this invention provide a few hundred picoliters of plasma within a few seconds. They also may be reused. Clogging is minimized and reversible. The sizes and velocities (100 $\mu$m wide and 100 $\mu$m/s) indicate a Reynolds number ($R_e$=plv/$\eta$) of about $10^{-2}$ so that the fluid is in a regime where viscosity dominates over inertia.

The magnitude of the pressure drop needed to obtain an average velocity, v, of a fluid with absolute viscosity, $\eta$, and density, p, through a circular channel (length, 1, diameter, d) can be calculated from Poiseuille's Law (Batchelor, G. K., *An Introduction to Fluid Dynamics*, Cambridge Univ. Press 1967), $$\frac{P}{l} = \frac{32\eta v}{d^2}$$

Using v=100 $\mu$m/sec and d=100 $\mu$m, we get a pressure drop equivalent to about 0.3 mm of $H_2O$ per cm of channel length. Since Poiseuille's equation is only strictly valid for circular flow channels and the channels of this invention are substantially V-shaped grooves, it can be considered only as an approximate relation between the variables represented.

When a liquid is introduced into a device there is at first an effective pressure, $P_{eff}=P_o+P_{st}$, equal to the sum of the applied pressure, $P_o$, and a pressure due to the surface tension, $$P_{st} = \frac{\gamma \cos\Theta}{r}.$$

$P_{st}$ is a function of the surface tension of the fluid, $\gamma$, the contact angle of the fluid with the surface, $\Theta$, and the radius of curvature of the fluid surface, r.

For hydrophilic surfaces, cos $\Theta$ is close to 1, and for small channels no applied pressure is needed to wet the device. This is referred to as "wetting by capillary action." However, once the device is completely wet, one has to worry about the surface tension at the exit area. In the device described in the example hereof, the radius of curvature of the fluid in the exit area was several millimeters, so that the pressure due to the surface tension was negligible.

With a channel width of 100 $\mu$m, $P_{st}$ is about 1 cm of $H_2O$, so surface tension on the exit channel is significant. However, using an etchant such as EPW F-Etch as described below, which attacks the {100} planes of silicon, means that the corners as etched are not as sharp as shown in FIG. 2. This results in a gradual widening of the channel to about 1 mm which reduces the effect of the surface tension.

This effect also occurs in the barrier region. Using an etchant that gives a vertical (90°) profile, instead of the 55° characteristic of the {100} planes of silicon, would require a pressure as large as one atmosphere to overcome the surface tension in a 0.1 $\mu$m gap.

Since this filter design is self-priming, it can be operated in two modes. In "one-shot mode," a drop (one $\mu$l) of blood contacts the entrance port. The blood is drawn down the channel and plasma is drawn through the filter without any applied pressure. This provides several nanoliters of plasma within a few seconds. Once fluid fills the device, flow stops. If no way is provided to flush this sample out of the device, it would have only one use.

The second mode, continuous flow mode, requires an applied pressure head. The relative pressure between the feed inlet, feed exit, and filtrate exit can be controlled to provide a continuous stream of filtrate or to induce some reverse flow through the filter which is useful for removing particles stuck on or near the barrier channel.

EXAMPLE

A three mask level process was used to fabricate a microfilter of this invention on a silicon wafer. The first level defined connection ports, which were etched completely through the wafer to the rear side of the silicon. The second level defined the fluid transport channels, and the third level defined the maximum size of particles which could flow through the filter.

Four inch chrome masks were made to these specifications by Photo Sciences, Inc. (Torrance, Calif.) and 3" wafers ({100}, n-type) with 500 nm of $SiO_2$ grown on them were used.

Wafers were cleaned in a Piranha bath ($H_2SO_4$ and $H_2O_2$) (2:1) before processing. A primer (HMDS spun on at 3000 rpm) was used to enhance photoresist adhesion. About one $\mu$m of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylenediamine, pyro-catechol, and water (EPW F-etch as described in Reisman, A., et al. (1979) J. Electrochem. Soc. 126:1406–1415) set up in a reflux boiling flask. This etch attacks the {100} planes of silicon at a rate of about 100 $\mu$m an hour. Fluid attachment ports were etched in the first step for about three hours. Photoresist was again applied, and the mask containing flow channels between fluid ports and the barrier region was exposed. The wafers were developed and etched in this second step for about one hour. Photoresist was applied once more and the mask containing the barrier region was exposed. The wafers were developed and etched in the final step for about one minute.

After final processing, the wafers were once again cleaned in a Piranha bath and rinsed in DI water. They were then diced into individual devices about 1 cm by 1 cm.

Anodic bonding according to Wallis, G. and Pomerantz, D. I (1969) J. Appl. Physics 40:3946–3949, was used to attach Pyrex glass to the silicon devices. One inch square pieces of Pyrex glass (100 $\mu$m thickness) from Esco Products Inc. (Oak Ridge, N.J.) were used. First, the silicon and Pyrex glass were immersed in a solution of $H_2O_2$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Testing was done by flowing dilute suspensions of fluorescent microspheres through the device. One drop of 16 $\mu$m diameter fluorescing microspheres (1% solids, from Duke Scientific, Palo Alto, Calif.) was added to 5 ml of DI water. A similar mixture of 2.6 $\mu$m diameter spheres was also prepared. The 16 $\mu$m spheres fluoresce in the green and the 2.6 $\mu$m diameter spheres fluoresce in the red, making them easily discernible by eye.

This mixture was introduced into the device, and observations were made using a Zeiss ICM-405 inverted microscope. Fluorescence of the spheres was observed using a silicon intensified target camera (SIT-66x, from Dage-MTI) and observations were recorded on video tape. Some images were also digitized using a frame grabber (Data Translation) and NIH Image software.

The pressures at the inlet port and at the exit port of the filtered liquid were controlled by filling a tube to the appropriate height with liquid. The pressures at the exit port of the unfiltered feed liquid was held constant to within a few mm of $H_2O$.

The experiment proceeded by first inserting a mixture of fluid and particles at the inlet port. Once this wet the entire device (one-shot mode), some particle build-up on the edge of the barrier channel was observed. Typically, some 16 $\mu$m spheres would build up along the barrier channel, but not to any significant depth.

The solution containing 2.6 $\mu$m spheres was then added to the inlet. These spheres freely flowed through the feed flow channel and some crossed the barrier channel.

The filter exit port was then pressurized to about half the pressure being put on the feed inlet. This resulted in a backflow across the barrier, quickly forcing the 16 $\mu$m spheres back into the flowstream where they were carried to the feed exit port.

The fluorescent spheres with a 16 micron diameter were immediately visible in the inlet port, as well as a few flowing along the feed flow channel and some pressed against the barrier channel. None passed through the barrier channel. After the introduction of 2.6 $\mu$m spheres, these smaller spheres were easily seen. Most flowed along the feed flow channel but some easily passed by the barrier which trapped the 16 $\mu$m spheres.

The preferred embodiments described above are illustrative rather than limiting of the invention. As will be readily understood by those skilled in the art, various materials, processes and parameters can be varied to achieve the objectives of this invention to provide a microfilter capable of providing analyzable quantities of particle-free liquid, and utilizing the principles of tangential flow past the barrier channel to reduce clogging, and sloped channel walls to overcome the effects of surface tension. The invention is limited only by the scope of the claims appended hereto.

We claim:

1. A microfilter useful for treating a feed liquid to separate liquid from particles contained therein comprising the following elements formed into the surface of a horizontal substrate:
    a) a feed inlet;
    b) a feed exit;
    c) a microfluidic feed flow channel having a minimum dimension sufficient to permit flow of the particles and liquid therethrough, disposed between and in fluid communication with the feed inlet and the feed exit;
    d) a microfluidic filtrate collection channel parallel to the feed flow channel;
    e) a single barrier channel parallel to, between, and in fluid communication with the feed flow channel and the filtrate collection channel; the barrier channel having a depth sufficiently small to permit flow of the liquid therethrough but not the particles;
    f) a filtrate exit in fluid communication with the filtrate collection channel; and
    g) a lid covering the surface of the horizontal substrate.

2. The microfilter of claim 1 also comprising a filtrate outlet channel connecting the filtrate collection channel and the filtrate exit.

3. The microfilter of claim 1 also comprising means for applying pressure to the flow of the feed liquid through the microfilter.

4. The microfilter of claim 1 having hydrophilic surfaces whereby the liquid flows through the microfilter from the feed inlet to the filtrate exit without the application of pressure.

5. The microfilter of claim 1 adapted for the separation of plasma from whole blood.

6. The microfilter of claim 1 wherein the feed flow channel and the filtrate collection channel are substantially V-shaped.

7. The microfilter of claim 2 wherein the feed flow channel, the filtrate collection channel and the filtrate outlet channel are substantially V-shaped.

8. The microfilter of claim 1 wherein the feed flow channel and the filtrate collection channel are approximately 100 microns wide.

9. The microfilter of claim 2 wherein the barrier channel has a smallest dimension of less than about 0.1 micron.

10. The microfilter of claim 1 wherein the substrate is a silicon wafer.

11. The microfilter of claim 10 wherein the channels are etched by an anisotropic etchant to provide gradual widening at the inlet and exits whereby flow therethrough by means of capillary action alone is facilitated.

12. The microfilter of claim 1 wherein the lid comprises a glass sheet.

13. The microfilter of claim 1 adapted to separate an analyzable quantity of plasma from one microliter of blood.

14. An analytical system comprising the microfilter of claim 1 and also comprising injection means for introducing the feed liquid into the feed inlet.

15. The microfilter of claim 1 comprising means in fluid communication with the filtrate exit for detecting the presence of an analyte in the filtrate.

16. The microfilter of claim 1 wherein the width of the barrier channel is greater than or about equal to the width of the feed flow channel.

17. The microfilter of claim 16 wherein the width of the barrier channel is about equal to the width of the feed flow channel.

18. A method for recovering a quantity of liquid separated from particles from a feed liquid containing said particles comprising introducing the feed liquid into the feed inlet of the microfilter of claim 1 and withdrawing separated liquid from the filtrate exit.

19. The method of claim 18 wherein the feed liquid is blood, the particles are blood cells, and the separated liquid is plasma.

20. The method of claim 19 wherein pressure is applied to the microfilter following withdrawal of separated liquid from the filtrate exit to clear the barrier channel of particles.

* * * * *

UNITED STATES PATENT AND TRADEMARK OFFICE
CERTIFICATE OF CORRECTION

PATENT NO. : 5,922,210

DATED : July 13, 1999

INVENTOR(S) : Brody et al.

It is certified that error appears in the above-identified patent and that said Letters Patent is hereby corrected as shown below:

In column 11, line 13, second line of claim 9, please delete "smallest dimension" and replace with --depth--.

Signed and Sealed this

Thirtieth Day of May, 2000

Attest:

Q. TODD DICKINSON

*Attesting Officer*  *Director of Patents and Trademarks*

UNITED STATES PATENT AND TRADEMARK OFFICE
CERTIFICATE OF CORRECTION

PATENT NO. : 5,922,210

DATED : July 13, 1999

INVENTOR(S) : Brody et al.

It is certified that error appears in the above-identified patent and that said Letters Patent is hereby corrected as shown below:

In column 11, line 13, second line of claim 9, please delete "smallest dimension" and replace with --depth--.

Signed and Sealed this

Thirteenth Day of February, 2001

*Attest:*

NICHOLAS P. GODICI

*Attesting Officer*     *Acting Director of the United States Patent and Trademark Office*